United States Patent [19]

Styles

[11] Patent Number: 4,903,584

[45] Date of Patent: Feb. 27, 1990

[54] DEODORIZING AIR VENT ATTACHMENT

[76] Inventor: Toni C. H. Styles, 1 Kipling Place, Barrie, Ontario, Canada, L4N 4W9

[21] Appl. No.: 273,488

[22] Filed: Nov. 21, 1988

[51] Int. Cl.$^4$ ................................................ A61L 9/00
[52] U.S. Cl. ........................................ 98/101; 98/109; 239/57; 239/60
[58] Field of Search ............ 98/101, 105, 109, DIG. 8; 239/34, 55, 56, 57, 60; 422/123, 124

[56] References Cited

U.S. PATENT DOCUMENTS

| | | | |
|---|---|---|---|
| 324,853 | 8/1885 | Laurier | 239/57 X |
| 1,729,119 | 9/1929 | Odean | 98/109 X |
| 2,203,552 | 6/1940 | Teevin | 98/109 X |
| 2,721,098 | 10/1955 | Mangels | 239/57 X |
| 4,523,870 | 6/1985 | Spector | 239/57 X |
| 4,617,517 | 10/1986 | Stein et al. | 239/57 X |

FOREIGN PATENT DOCUMENTS 636472  3/1962  Italy ...................................... 239/57

Primary Examiner—Harold Joyce

[57] ABSTRACT

A deodorizer receiving device which is attachable to an air vent fitting. The device comprises a vent fitting mounting surface and a deodorant holding region supported by the mounting surface. The deodorant holding region is itself ventilated for air dispersal of the deodorant supported in the holding region.

1 Claim, 3 Drawing Sheets

DEODORIZING AIR VENT ATTACHMENT

FIELD OF THE INVENTION

The present invention relates to a deodizer-type device which is designed for direct attachment at the fitting of a vent opening thereby using the natural air flow of the air through the vent to carry the deodorizer effect into a room.

BACKGROUND OF THE INVENTION

Most deodorizers are nothing more than stationary units provided with a scented deodorant carried by the natural convection currents within a room. However, with these stationary type units, one is generally only able to notice the effects within several feet of the unit. In most cases, the convection currents are not strong enough to carry the deodorizing effects any significant distance from the unit.

In some instances, people will actually use fans positioned beside the stationary units to get a better movement of air past the deodorizer.

Device which has been specifically designed to combat bacteria in the air are electronic air exchangers or ionizers. However, these devices are expensive and are not capable of providing a deodorizing effect to the surrounding air.

SUMMARY OF THE PRESENT INVENTION

The present invention provides a deordorizer receiving device which is designed specifically for attachment to an air vent fitting. The device comprises a vent fitting mounting surface and a deodorant holding region supported by the mounting surface. The deodorant holding region is specifically designed to receive different types of solid deodorants and is ventilated for air dispersal using the air passing through the air vent to carry the deodorizing effects from the deodorant into a room.

The device of the present invention does not require the use of any additional fans or the like, because as noted above, it takes advantage of the existing air flow through a vent. Furthermore, the device of the present invention which is particularly suited for receiving a standard scented fabric cloth is inexpensive and easy to manufacture while being extremely effective.

BRIEF DESCRIPTION OF THE DRAWINGS

The above as well as other advantages and features of the present invention will be described in greater detail according to the preferred embodiments of the present invention in which.

DETAILED DESCRIPTION ACCORDING TO THE PREFERRED EMBODIMENTS OF THE PRESENT INVENTION IN WHICH

Figure 1:
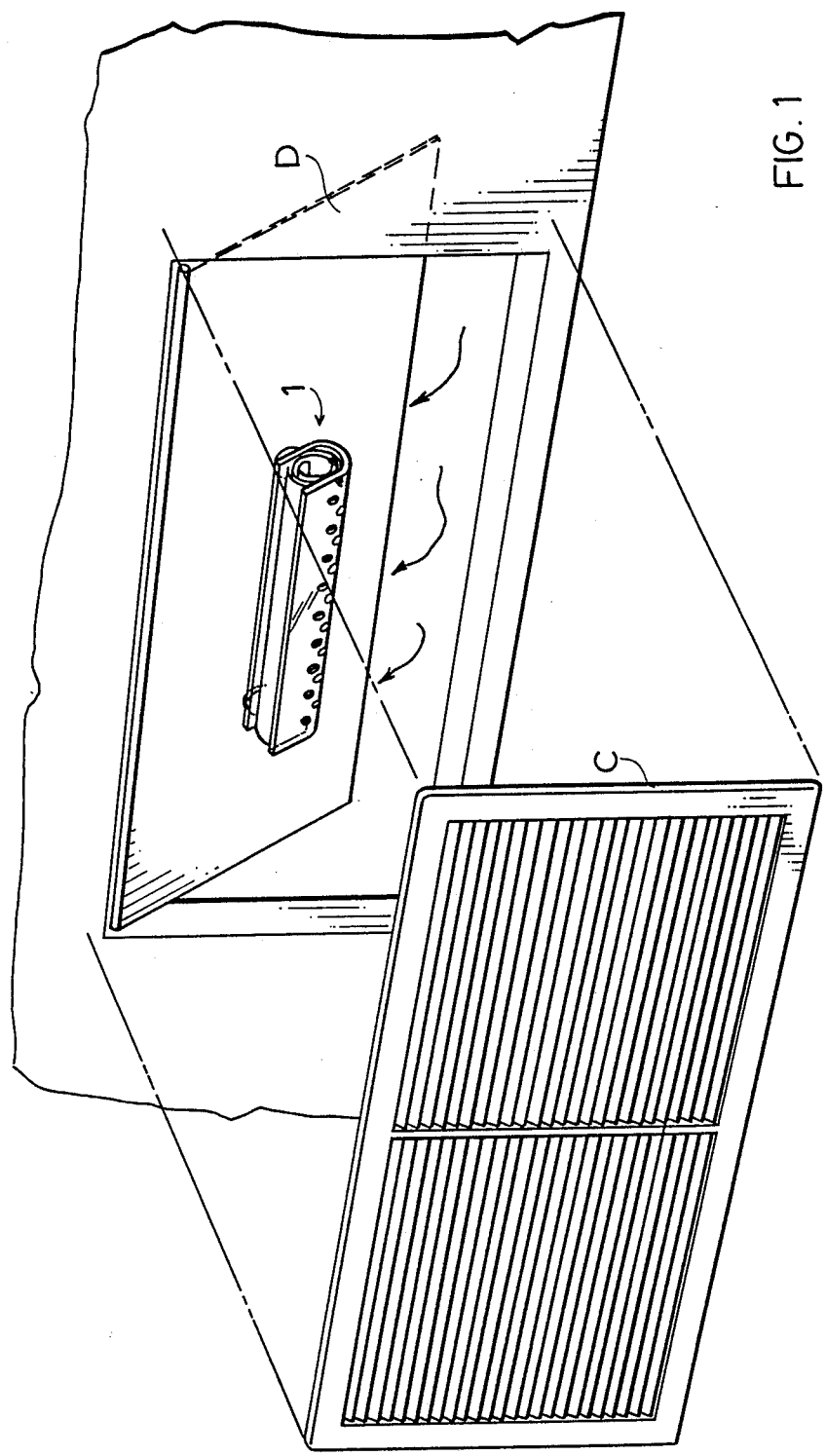
FIG. 1 shows an air vent set up provided with a deodorizer receiving device secured in an operating position.

FIG. 1 shows, with the exception of device 1, a relatively standard air vent set up. This air vent set up includes a fitting for the vent opening comprising a vent flow damper D which is movable between a fully closed and a fully opened position and a vent cover C to the outside surface of the vent opening.

FIG. 1 shows the damper D in an opened position allowing a flow of air through the vent opening past the grilled cover C. The vent opening is on the positive or blower side of the air ventilation system in a house or building so that the air passes out of the vent into a room. This air may be used for heating or cooling of the room or it may be non-heat treated air for venting purposes only.

As noted above, the unique feature of the set up of Figure is in the inclusion of device 1 attached directly to the damper D. This device is best seen having reference to FIG. 3 of the drawings and is constructed as described immediately below.

Device 1 as shown has a generally U-shaped configuration. This configuration comprises a rear wall 7, a forward wall 3 and a lower dished region 5 joining the rear and forward walls. The dished region in cooperation with both the rear and forward walls forms a trough for receiving a solid deodorizer. The shape as shown is particularly useful for receiving a cloth-type deodorizer such as a BOUNCE ™ sheet 11 which is sold for the drying of clothes. However, the trough-like holding region of device 1 is specifically dimensioned such that sheet 11 when rolled upon itself as shown in FIG. 2 of the drawings can be simply dropped down into and supported by the trough.

Provided to the rear of the device are a pair of magnets 9, one at either end of mounting surface 7. In accordance with standard practice damper D has a metallic construction to magnetically secure device 1 through the attaching magnets 9. The positioning of the magnets to each end of the device prevents it from tipping or tilting sideways after it has been attached to the damper.

Figure 3:
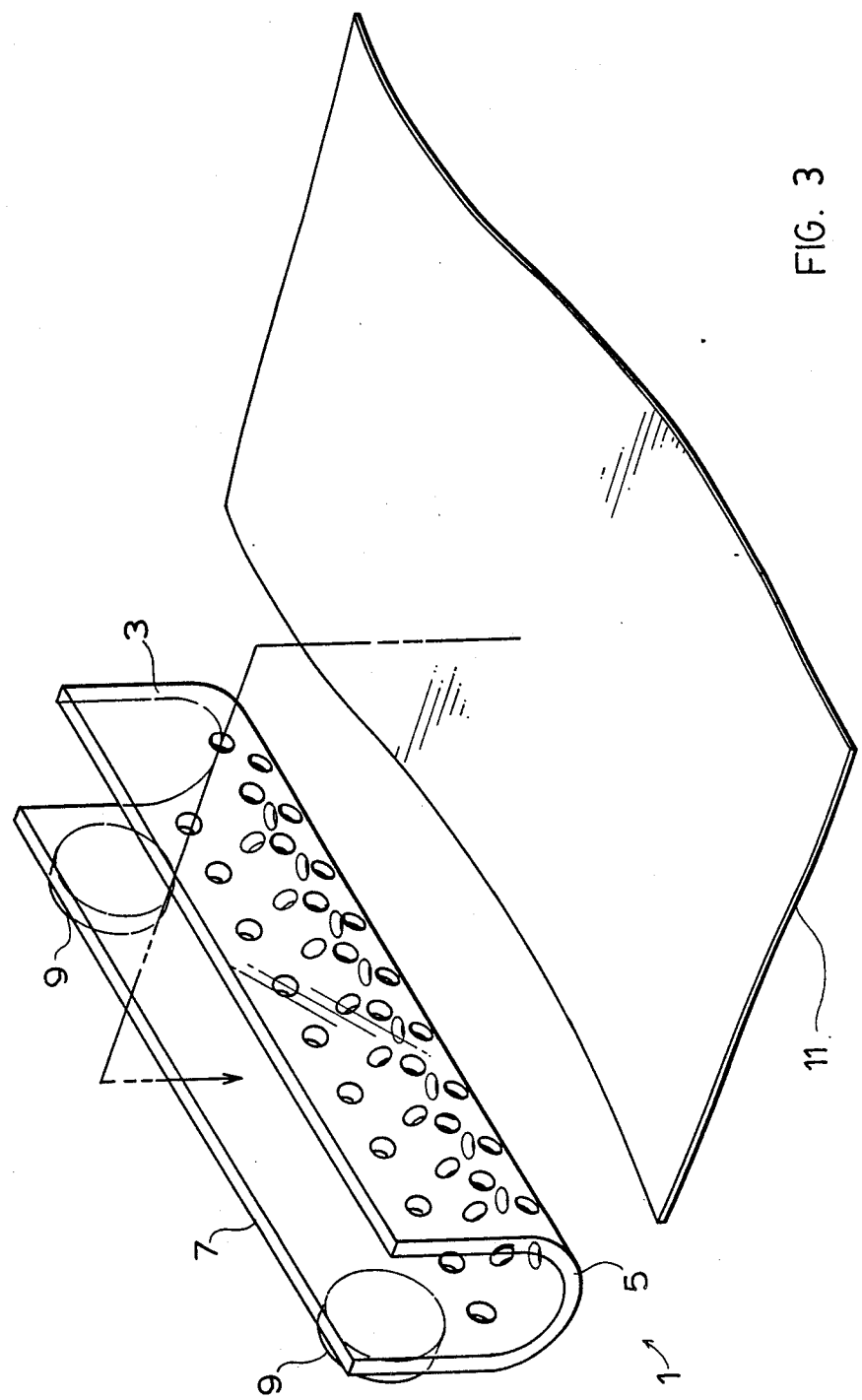
FIG. 3 is an enlarged perspective view of the device itself ready for fitting with a deodorizer fabric cloth.

As will be clearly seen in FIG. 3 of the drawings, the deodorizer receiving trough region is ventilated and in particular is provided with venting holes extending part way up both the back and front walls 7 and 3 respectively and all along the lower wall or dished region 5.

Figure 2:
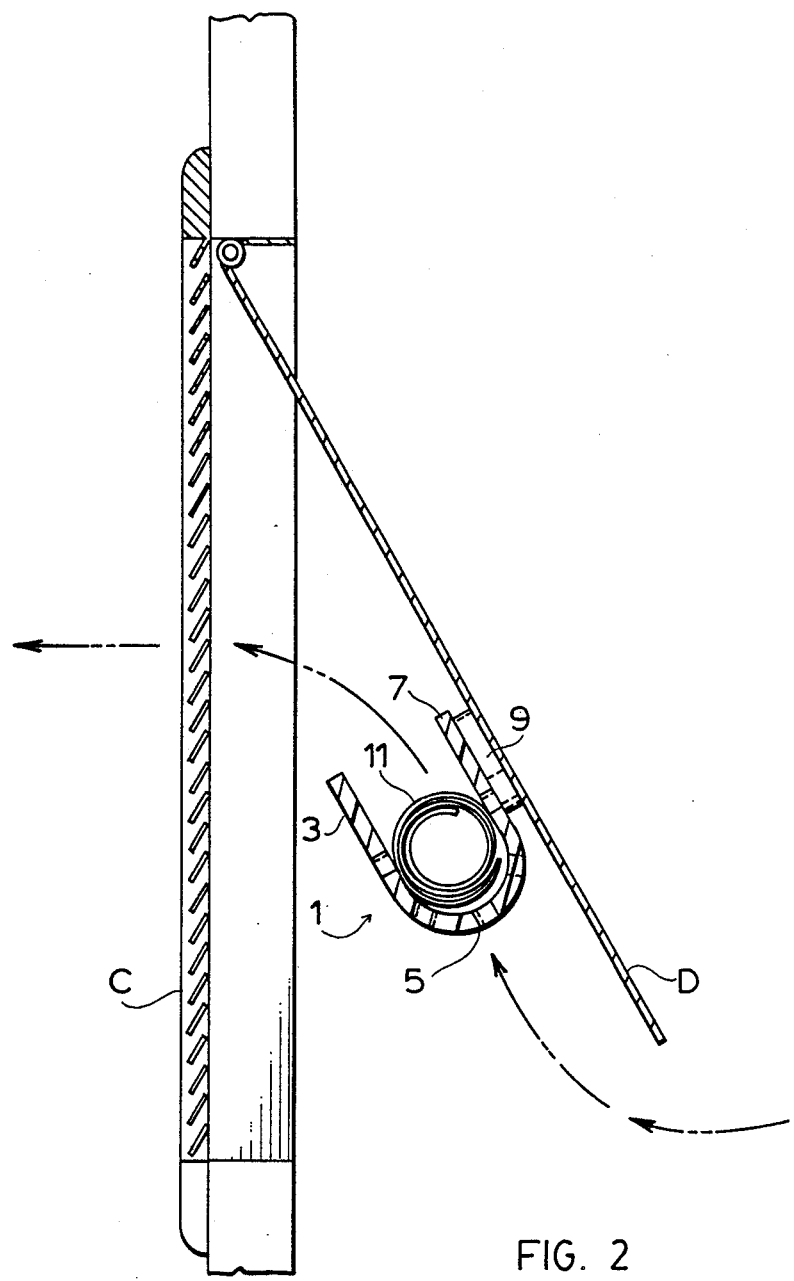
FIG. 2 is an enlarged side view of the set up of FIG. 1 showing the ventilation effects through the deodorizer receiving device.

The operation of device 1 is best described having reference to FIG. 2 of the drawings. Here it will be seen that the device is attached through magnets 9 directly to the front surface of the damper. When the damper is open, the air flows through the air ducting (not shown) and upwardly past the front of the damper where device 1 is attached. This air flow therefore is naturally carried around and through device 1 into which the solid deodorant such as rolled sheet 11 is fitted. Again, note that the size of the trough region is such that the sheet when rolled upon itself fits relatively snugly into the device so that the air flow will not dislodge the sheet. This same air flow, which occurs regardless of whether or not device 1 is in position is used to carry the deodorizing effects from the deodorant held in device 1 outwardly into the room.

The description above relates to the use of a sheet-type deodorizer. However, it is to be appreciated that other types of solid deodorants can equally as well be used. For example, another particularly good type of solid deodorizer is a sponge rubber body shaped to fit in the trough and lightly sprinkled with a liquid deodorant which soaks into the sponge body.

One particularly unique advantage resulting from the use of the deodorizer receiving device of the present invention is that because of its attachment to damper D, the device is positioned to the inside of the vent cover C and therefore, both out of sight and hidden behind the vent cover. Again, in accordance with standard practice the vent cover itself can be simply pulled out of its position shown in FIG. 2 to gain access to the damper and permit the attachment of device 1 in the FIG. 2 position. Furthermore for the most part, device 1 once secured does not affect the opening or closing of the damper.

Although various preferred embodiments of the invention have been described in detail, it will be appreciated by those skilled in the art that variations may be made without departing from the spirit of the invention or the scope of the appended claims.

The embodiments of the invention in which an exclusive property or privilege is claimed are defined as follows:

1. An in-building air vent set up comprising a vent opening, a damper plate at and movable to different angles for opening and closing said vent opening, and a deodorizer receiving device secured to and movable with said damper plate, said deodorizer device comprising a trough with an open side for receiving said deodorizer with said trough being ventilated for air dispersal of deodorant from the deodorizer, said deodorizer comprising a deodorant sheet rolled upon itself and fitted within said trough, said sheet having a memory urging said sheet to unroll whereby said sheet is frictionally engaged in said trough.

* * * * *